United States Patent
Nugent

(10) Patent No.: US 9,959,715 B2
(45) Date of Patent: May 1, 2018

(54) SLEEP INHIBITION ASSEMBLY

(71) Applicant: Mark Nugent, Franklin, IN (US)

(72) Inventor: Mark Nugent, Franklin, IN (US)

( * ) Notice: Subject to any disclaimer, the term of this patent is extended or adjusted under 35 U.S.C. 154(b) by 0 days. days.

(21) Appl. No.: 15/185,116

(22) Filed: Jun. 17, 2016

(65) Prior Publication Data
US 2017/0365138 A1 Dec. 21, 2017

(51) Int. Cl.
G08B 6/00 (2006.01)
A61H 1/00 (2006.01)
A61M 21/00 (2006.01)

(52) U.S. Cl.
CPC .............. G08B 6/00 (2013.01); A61M 21/00 (2013.01); A61M 2021/0022 (2013.01); A61M 2021/0083 (2013.01)

(58) Field of Classification Search
None
See application file for complete search history.

(56) References Cited

U.S. PATENT DOCUMENTS

| 2,747,038 A | 5/1956 | Perkovich | |
|---|---|---|---|
| 4,555,697 A | 11/1985 | Thackrey | |
| 5,684,461 A | 11/1997 | Jones | |
| 6,183,427 B1 * | 2/2001 | Ishii | A61M 21/00 601/139 |
| 7,126,485 B2 | 10/2006 | Cece et al. | |
| D590,991 S | 4/2009 | Hon | |
| 8,610,585 B1 | 12/2013 | Kielbasa et al. | |
| 8,851,887 B1 * | 10/2014 | Ostreicher | A61C 19/06 433/215 |
| 2015/0346496 A1 * | 12/2015 | Haddick | G02B 27/0176 359/630 |

* cited by examiner

Primary Examiner — Joseph Feild
Assistant Examiner — John Mortell

(57) ABSTRACT

A sleep inhibition assembly for inhibiting a driver from falling asleep includes a housing that may be manipulated. A vibration unit is coupled to the housing and the vibration unit vibrates the housing. The vibration unit may be placed in a mouth. Thus, the vibration unit may inhibit a driver from falling asleep.

9 Claims, 4 Drawing Sheets

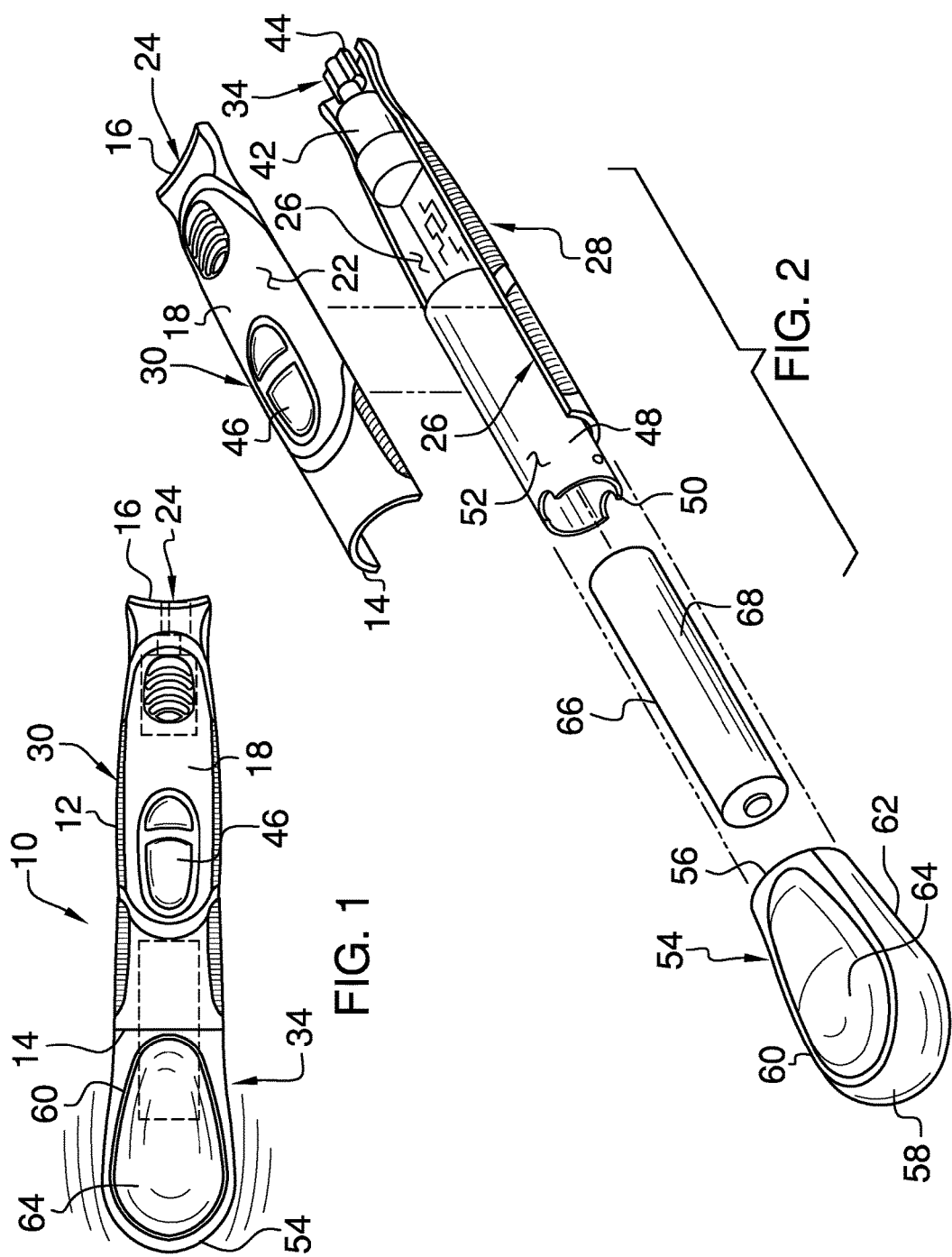

SLEEP INHIBITION ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIE THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to inhibition devices and more particularly pertains to a new inhibition device for inhibiting a driver from falling asleep.

BRIEF SUMMARY OF THE INVENTION

An embodiment of the disclosure meets the needs presented above by generally comprising a housing that may be manipulated. A vibration unit is coupled to the housing and the vibration unit vibrates the housing. The vibration unit may be placed in a mouth. Thus, the vibration unit may inhibit a driver from falling asleep. The driver may be an over the road truck driver or the like.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 1 is a top view of a sleep inhibition assembly according to an embodiment of the disclosure.

FIG. 2 is an exploded perspective view of an embodiment of the disclosure.

DETAILED DESCRIPTION OF THE INVENTION

Figure 3:
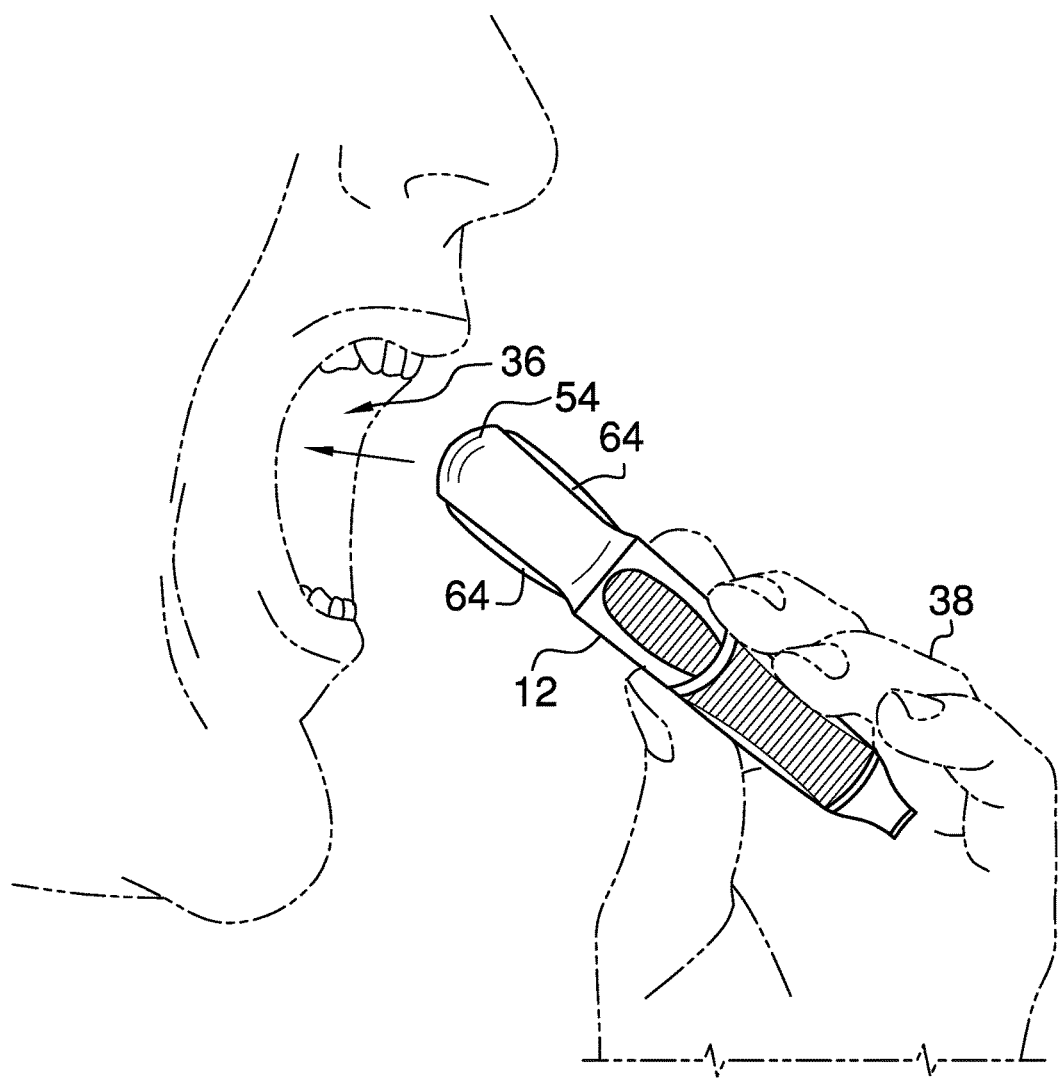
FIG. 3 is a perspective in-use view of an embodiment of the disclosure.
Figure 4:
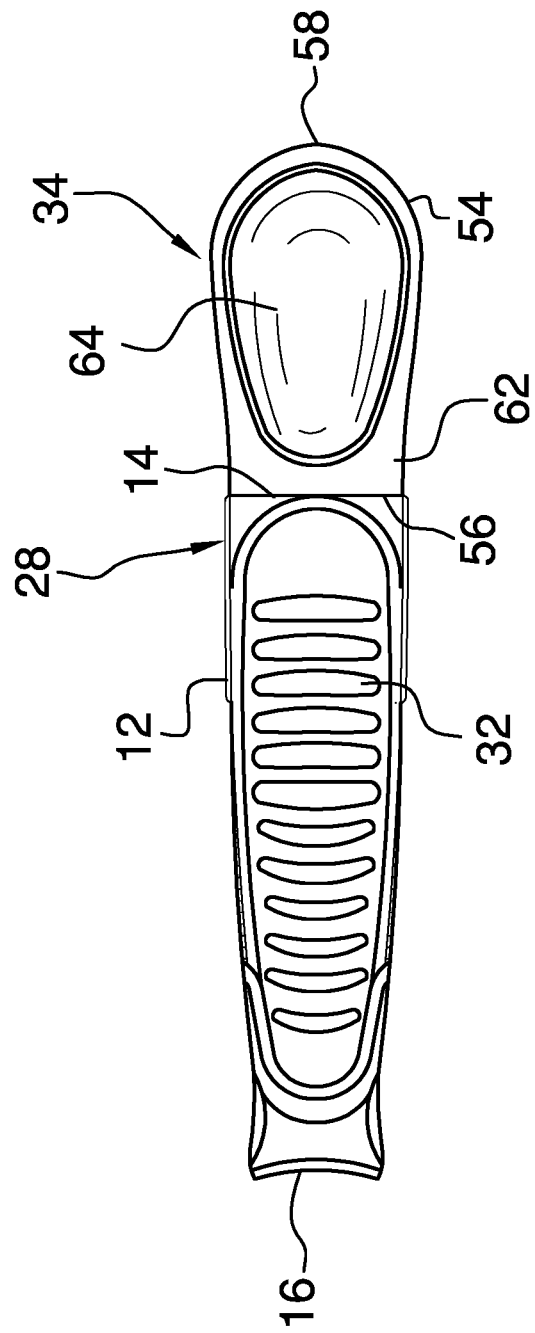
FIG. 4 is a bottom view of an embodiment of the disclosure.
Figure 5:
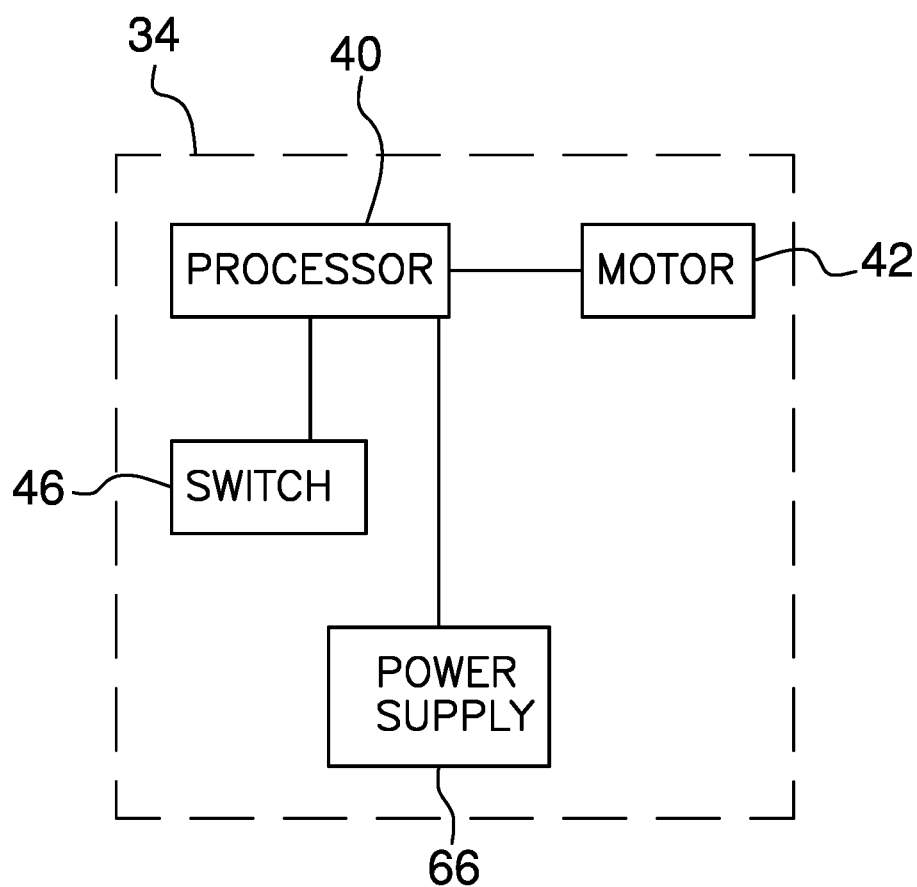
FIG. 5 is a schematic view of an embodiment of the disclosure.

With reference now to the drawings, and in particular to FIGS. 1 through 5 thereof, a new inhibition device embodying the principles and concepts of an embodiment of the disclosure and generally designated by the reference numeral 10 will be described.

As best illustrated in FIGS. 1 through 5, the sleep inhibition assembly 10 generally comprises a housing 12 that may be manipulated. The housing 12 has a first end 14, a second end 16 and an outer wall 18 extending therebetween. The outer wall 18 has an inside surface 20 and an outside surface 22. The first end 14 is open and the housing 12 is substantially hollow.

The outer wall 18 is continuous such that the housing 12 is substantially cylindrically shaped. The housing 12 is flattened to adjacent to the second end 16 to define a tail 24 of the housing 12. The outer wall 18 has a longitudinal cut 26. The longitudinal cut 26 defines a first half 28 of the housing 12 that is matable to a second half 30 of the housing 12.

A grip 32 is coupled to the housing 12. Thus, the grip 32 enhances gripping the housing 12. The grip 32 is positioned on the outside surface 22 corresponding to the first half 28 of the housing 12. The grip 32 may be comprised of a resiliently compressible material. Additionally, the grip 32 may be textured.

A vibration unit 34 is provided. The vibration unit 34 is coupled to the housing 12 and the vibration unit 34 selectively vibrates the housing 12. The vibration unit 34 may be placed in a mouth 36. Thus, the vibration unit 34 may inhibit a driver 38 from falling asleep.

The vibration unit 34 comprises a processor 40 that is positioned within the first half 28 of the housing 12. The processor 40 may comprise an electronic processor 40 or the like. A motor 42 is coupled to the inside surface 20 corresponding to the first half 28 of the housing 12. The motor 42 is positioned closer to the second end 16 than the first end 14 corresponding to the first half 28. The motor 42 is electrically coupled to the processor 40. The motor 42 may comprise an electrical motor 42 or the like.

A weight 44 is provided. The weight 44 is rotatably coupled to the motor 42. Thus, the motor 42 rotates the weight 44 when the motor 42 is turned on. The weight 44 is offset with respect to a longitudinal axis extending through the motor 42. Thus, the weight 44 transfers vibration into the housing 12 when the motor 42 is turned on.

A switch 46 is provided. The switch 46 is coupled to the outside surface 22 corresponding to the second half 30 of the housing 12 and the switch 46 may be manipulated. The switch 46 is electrically coupled to the processor 40. The switch 46 turns the motor 42 on and off.

A sleeve 48 is provided. The sleeve 48 is coupled to the inside surface 20 corresponding to the first half 28 of the housing 12. The sleeve 48 extends outwardly from the first end 14 corresponding to the first half 28 of the housing 12. The sleeve 48 has a distal end 50 with respect to the first half 28 of the housing 12. The sleeve 48 has an exterior surface 52.

A head 54 is provided. The head 54 has a primary end 56, a secondary end 58, a top side 60 and a bottom side 62. The primary end 56 is open and the secondary end 58 is concavely arcuate with respect to the primary end 56. Thus, the head 54 is substantially tear drop shaped.

The primary end 56 insertably receives the distal end 50 of the sleeve 48. The head 54 frictionally engages the exterior surface 52 of the sleeve 48. Thus, the head 54 is removably coupled to the housing 12. Thus, the head 54 vibrates when the motor 42 is turned on. The head 54 may be placed in a mouth 36 thereby facilitating the head 54 to vibrate the mouth 36. Thus, the head 54 may stimulate the driver 38 thereby inhibiting the driver 38 from falling asleep.

A pair of pads 64 is provided. Each of the pads 64 is coupled to an associated one of the top side 60 and the bottom side 62 of the head 54. Each of the pads 64 is comprised of a resiliently compressible material. Thus, each of the pads 64 may enhance comfort of the head 54 with respect to the mouth 36.

A power supply 66 is provided. The power supply 66 is removably positioned in the sleeve 48. The power supply 66 is electrically coupled to the processor 40 when the power supply 66 is positioned in the sleeve 48. The power supply 66 comprises at least one battery 68.

In use, the switch 46 is manipulated to turn the motor 42 on. The motor 42 rotates the weight 44 and the weight 44 vibrates the housing 12 and the head 54. The head 54 is placed in the driver 38's mouth 36. Thus, the head 54 vibrates the user's mouth 36 thereby stimulating the driver 38 while the driver 38 is driving. The stimulation inhibits the driver 38 from falling asleep while the driver 38 is driving.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A sleep inhibition assembly being configured to inhibit a driver from falling asleep, said assembly comprising:
   a housing being configured to be manipulated, said housing having a first end, a second end and an outer wall extending therebetween, said outer wall having an inside surface and an outside surface, said first end being open, said housing being substantially hollow, said outer wall being continuous such that said housing is substantially cylindrically shaped;
   a head coupled to and extending from said first end of said housing, said head being configured to be placed in a mouth; and
   a vibration unit being coupled to said housing wherein said vibration unit is configured to vibrate said housing, said vibration unit being configured to be placed in a mouth thereby facilitating said vibration unit to inhibit a driver from falling asleep, said vibration unit comprising
      a motor being coupled to said inside surface of said housing, said motor being positioned closer to said second end than said first end, and
      a weight being rotatably coupled to said motor such that said motor rotates said weight when said motor is turned on, said weight being offset with respect to a central longitudinal axis extending through said motor wherein said weight is configured to transfer vibration into said housing when said motor is turned on, said weight being positioned at said second end of said housing wherein said weight is oppositely positioned relative to said head.

2. The assembly according to claim 1, wherein said second end is flattened to define a tail of said housing, said outer wall having a longitudinal cut to define a first half of said housing being matable to a second half of said housing.

3. The assembly according to claim 2, further comprising a grip being coupled to said housing wherein said grip is configured to enhance gripping said housing, said grip being positioned on said outside surface corresponding to said first half of said housing.

4. The assembly according to claim 1, further comprising a switch being coupled to said outside surface corresponding to said second half of said housing wherein said switch is configured to be manipulated, said switch being electrically coupled to said motor such that said switch selectively turns said motor on and off.

5. The assembly according to claim 2, further comprising a sleeve being coupled to said inside surface corresponding to said first half of said housing, said sleeve extending outwardly from said first end corresponding to said first half of said housing, said sleeve having a distal end with respect to said first half of said housing, said sleeve having an exterior surface.

6. The assembly according to claim 5, further comprising said head having a primary end, a secondary end, a top side and a bottom side, said primary end being open, said secondary end being concavely arcuate with respect to said primary end, said primary end insertably receiving said distal end of said sleeve such that said head is removably coupled to said housing wherein said head is configured to vibrate when said motor is turned on.

7. The assembly according to claim 6, further comprising a pair of pads, each of said pads being coupled to an associated one of said top side and said bottom side of said head, each of said pads being comprised of a resiliently compressible material wherein each of said pads is configured to enhance comfort of said head with respect to the mouth.

8. The assembly according to claim 5, further comprising a power supply being removably positioned in said sleeve, said power supply being electrically coupled to said motor when said power supply is positioned in said sleeve, said power supply comprising at least one battery.

9. A sleep inhibition assembly being configured to inhibit a driver from falling asleep, said assembly comprising:

a housing being configured to be manipulated, said housing having a first end, a second end and an outer wall extending therebetween, said outer wall having an inside surface and an outside surface, said first end being open, said housing being substantially hollow, said outer wall being continuous such that said housing is substantially cylindrically shaped, said second end being flattened to define a tail of said housing, said outer wall having a longitudinal cut to define a first half of said housing being matable to a second half of said housing;

a grip being coupled to said housing wherein said grip is configured to enhance gripping said housing, said grip being positioned on said outside surface corresponding to said first half of said housing;

a sleeve being coupled to said inside surface corresponding to said first half of said housing, said sleeve extending outwardly from said first end corresponding to said first half of said housing, said sleeve having a distal end with respect to said first half of said housing, said sleeve having an exterior surface, a head having a primary end, a secondary end, a top side and a bottom side, said primary end being open, said secondary end being concavely arcuate with respect to said primary end, said primary end insertably receiving said distal end of said sleeve such that said head is removably coupled to said housing extending from said second end of said housing wherein said head is configured to be placed in a mouth, a pair of pads, each of said pads being coupled to an associated one of said top side and said bottom side of said head, each of said pads being comprised of a resiliently compressible material wherein each of said pads is configured to enhance comfort of said head with respect to the mouth, and a vibration unit being coupled to said housing wherein said vibration unit is configured to vibrate said housing, said vibration unit being configured to be placed in a mouth thereby facilitating said vibration unit to inhibit a driver from falling asleep, said vibration unit comprising:

a processor being positioned within said first half of said housing, a motor being coupled to said inside surface corresponding to said first half of said housing, said motor being positioned closer to said second end than said first end corresponding to said first half, said motor being electrically coupled to said processor, a weight being rotatably coupled to said motor such that said motor rotates said weight when said motor is turned on, said weight being offset with respect to a longitudinal axis extending through said motor wherein said weight is configured to transfer vibration into said housing when said motor is turned on, said weight being positioned at said second end of said housing, a switch being coupled to said outside surface corresponding to said second half of said housing wherein said switch is configured to be manipulated, said switch being electrically coupled to said processor such that said switch turns said motor on and off, and a power supply being removably positioned in said sleeve, said power supply being electrically coupled to said processor when said power supply is positioned in said sleeve, said power supply comprising at least one battery.

* * * * *